United States Patent [19]
Watanabe et al.

[11] 4,343,899
[45] Aug. 10, 1982

[54] PROCESS FOR PRODUCING STABLE AQUEOUS SOLUTION OF ACRYLAMIDE OR METHACRYLAMIDE

[75] Inventors: Ichiro Watanabe; Yoshiaki Satoh, both of Yokohama, Japan

[73] Assignee: Nitto Chemical Industry Co., Ltd., Tokyo, Japan

[21] Appl. No.: 120,960

[22] Filed: Feb. 13, 1980

[30] Foreign Application Priority Data

Feb. 13, 1979 [JP] Japan .................................. 54/14276

[51] Int. Cl.$^3$ .............................................. C12P 13/02
[52] U.S. Cl. .................................... 435/129; 435/227; 435/843; 435/872
[58] Field of Search ................................ 435/129, 227

[56] References Cited

U.S. PATENT DOCUMENTS 4,001,081 1/1977 Commeyras et al. ............... 435/129

Primary Examiner—Alvin E. Tanenholtz
Attorney, Agent, or Firm—Sughrue, Mion, Zinn, Macpeak & Seas

[57] ABSTRACT

This invention is a process for producing a stable aqueous solution of acrylamide or methacrylamide by subjecting acrylonitrile or methacrylonitrile in water to the action of microorganisms having a nitrilasic activity, which is characterized in that said microorganisms are treated with a water-soluble dialdehyde to thereby inhibit polymerization of the acrylamide or methacrylamide produced.

9 Claims, No Drawings

PROCESS FOR PRODUCING STABLE AQUEOUS SOLUTION OF ACRYLAMIDE OR METHACRYLAMIDE

BACKGROUND OF THE INVENTION

1. Field of the Invention

This invention relates to a process for obtaining acrylamide or methacrylamide as a stable aqueous solution without polymerization in producing acrylamide or methacrylamide using microorganisms.

2. Description of Prior Art

The use of microorganisms having a nitrilasic activity for hydrolyzing acrylonitrile or methacrylonitrile (hereinafter simply referred to as (meth)acrylonitrile) to produce acrylamide or methacrylamide (hereinafter simply referred to as (meth)acrylamide) has been known. Such a process is described in U.S. Pat. No. 4,001,081. As such microorganisms, bacteria of the genera Bacillus, Bacteridium in the sense of Prevot, Micrococcus and Brevibacterium in the sense of Bergey, etc., have been used and the inventors have also used microorganisms belonging to the genera Corynebacterium and Nocardia, described in Japanese Patent Application (OPI) No. 129190/79.

In producing (meth)acrylamide from (meth)acrylonitrile using these microorganisms, cells of these microorganisms act on (meth)acrylonitrile directly or after immobilizing them with polyacrylamide gel, etc. in an aqueous medium (for example, water, physiological saline, buffer solution, etc.). The reaction is usually conducted under the conditions of a substrate ((meth)acrylonitrile) concentration of about 1 to 10 wt%, a cell concentration of about 1 to 10 wt%, a pH of 7 to 9, at 25° to 30° C. for 0.5 to 10 hours so as to proceed the enzymatic reaction smoothly.

In the field of microbial reactions, batchwise or continuous column processes have recently been proposed using immobilized cells prepared by forming microbial cell particles which is advantageous from the point of view of the cell separation from a reaction solution, the availability of repeated use of the cells, and increasing enzyme stability. Such techniques are also useful in the process of producing (meth)acrylamide using microorganisms in the present invention.

However, a (meth)acrylamide aqueous solution produced using microorganisms is unstable and so susceptible to polymerization that concentration is difficult and, in addition, in a continuous column process, the (meth)acrylamide produced often polymerizes during hydrolysis which prevents smooth operation. The addition of known polymerization inhibitors such as methoxyquinone, copper salt, etc. might be considered but, with a (meth)acrylamide aqueous solution produced through microbial reaction, sufficient effects of the inhibitors cannot be attained unless these polymerization inhibitors are used in large amounts. Addition of such inhibitors in large amounts adversely affects the microbial reaction and seriously deteriorates the quality of the (meth)acrylamide aqueous solution.

SUMMARY OF THE INVENTION

As a result of various investigations to remove the above-described defects, the inventors have discovered that a stable (meth)acrylamide aqueous solution can be obtained in high purity without polymerization upon production or concentration of the (meth)acrylamide solution, by treating the microorganisms with a water-soluble dialdehyde before feeding them to the reaction system of (meth)acrylonitrile and water. Thus, many of the problems accompanying the use of microbial cells are overcome.

The mechanism of preventing polymerization of the (meth)acrylamide aqueous solution is not completely clear, but it may be that the water-soluble dialdehyde undergoes a crosslinking reaction with the microbial cells and, at the same time, it reacts with some polymerization-accelerating material existing within the cells to fix it within the cells, thus stopping its function and preventing it from being extracted from the cells.

DETAILED DESCRIPTION OF THE INVENTION

As the microorganisms used in the present invention, any microorganism having the ability to hydrolyze (meth)acrylonitrile to (meth)acrylamide can be used irrespective of its taxonomical position. However, particularly preferable are strain N-771 of the genus Corynebacterium (FERM-P No. 4445) Fermentation Research Institute, Agency of Industrial Science and Technology, Japan, strain N-774 of the genus Corynebacterium FERM-P No. 4446), and strain N-775 of the genus Nocardia (FERM-P No. 4447), described in Japanese Patent Application No. 35,818/78. Reference can also be made to U.S. Pat. No. 4,001,081 for suitable bacteria such as the genus Bacteridium in the sense of Prevot, the genus Micrococcus and Brevibacterium in the sense of Bergy. These suitable bacteria include the strains registered at the Central Bureau voor Schimmelcultures in Delft under the numbers C211 CBS 499.74, R312 CBS 717.73, B222 CBS 498.74, A111 CBS 497.74, R341 CBS 496.74, R340 CBS 495.74, R332 CBS 494.74.

In the case of immobilizing these microorganisms immobilization can be conducted according to any conventional process with an entrapping process using an acrylamide series polymer being particularly preferred. The term "acrylamide series polymer" as used herein is a polymer containing acrylamide, methacrylamide, or the like as a major component and, if necessary, an ethylenically unsaturated monomer copolymerizable with acrylamide, methacrylamide, or the like. Immobilization can be conducted by suspending the aforesaid microbial cells in an aqueous medium containing a monomer or monomers like acrylamide and a cross-linking agent like N,N-methylenebisacrylamide, and conducting polymerization at a pH of about 5 to 10, preferably 6 to 8, and at a temperature of about 0° to 30° C., preferably 0° to 15° C., using a polymerization initiator, thus causing gelation. The content of microorganisms in the polymerization reaction solution varies depending upon the kind and the state of microorganisms used, but is typically about 0.1 to 50 wt%, preferably 1 to 20 wt%. The content of monomers in the polymerization reaction solution is about 2 to 30 wt%, preferably about 5 to 20 wt%.

The water-soluble dialdehyde treatment is carried out either on intact cells or immobilized cells. To be specific, these microbial cells (in the case of immobilized cells, after pulverizing to a suitable size) are suspended in a buffer solution such as 0.05 to 0.5 M phosphate solution, and a water-soluble dialdehyde is added thereto in an amount of about 0.1 to 10.0 wt%, preferably 0.5 to 5.0 wt%, based on the weight of dry cells. The reaction is conducted at a pH of about 5 to 10, preferably 6 to 8, at a temperature of about 0° to 30° C., preferably about 0° to 15° C., for 0.5 to 3 hours under stirring. In addition, immobilization of water-soluble dialdehyde treated cells can also be conducted after treating the cell suspension with the dialdehyde.

Conditions selected specifically for the above-described treatments are determined considering the retention of enzymatic activity of microbial cells, inhibition of polymerization, economical advantages, etc.

The dialdehydes used in the present invention preferably have a solubility in water of 5 wt% or more at 20° C. Representative of the suitable dialdehydes are glyoxal, malondialdehyde, glutraldehyde, pimelic dialdehyde, dialdehyde starch, etc. Among these dialdehydes, glyoxal and glutaraldehyde are commercially available and preferred.

In producing an aqueous solution of (meth)acrylamide, the aforesaid dialdehyde-treated microbial cells (in the case of using immobilized cells, particles of suitable size) are filled in a reactor or a column, and are brought into contact with a (meth)acrylonitrile aqueous solution under the aforesaid conditions. The reaction temperature is preferably about 0° to 15° C. depending on retention of enzymatic activity. Additionally, the conversion of the reaction can be controlled by selecting the amount of cells, reaction time, flow rate of the substrate, and the like. Therefore, selection of proper conditions enables one to conduct the reaction conversion almost completely.

In the reaction using dialdehyde-treated microorganisms as described above, the continuous column process does not involve such troubles as that reaction is stopped due to polymerization and can be conducted smoothly. In addition, concentration of the reaction solution can be conducted without polymerization. Thus, there can be obtained a (meth)acrylamide aqueous solution having the aforesaid stability to polymerization.

The present invention will now be described in more detail by reference to the following Examples. Additionally, all parts and percents in the Examples are by weight. (Meth)acrylonitrile and (meth)acrylamide in the reaction solution were determined through gas chromatography, and polymerization in the (meth)acrylamide aqueous solution was checked by whether the solution became turbid or not upon addition of methanol with the naked eye.

EXAMPLE 1 AND COMPARATIVE EXAMPLE 1

0.2 part of a 50% glutaraldehyde aqueous solution and 59.8 parts of a 0.05 M phosphate buffer solution were added to 40 parts of washed microbial cells (water content: 75%) of strain N-774 prepared by aerobic culture using a culture medium (pH: 7.2) containing 1% glucose, 0.5% peptone, 0.3% yeast extract, and 0.3% malt extract, and stirred at 10° C. for 1 hour to react, thus dialdehyde-treatment being conducted. After completion of the reaction, cells were separated from the cell suspension by centrifugation, washed twice with 0.05 M phosphate buffer (pH: 8.0), then again centrifuged to obtain about 40 parts of pasty cells (water content: 75%).

8 parts of the resulting cell paste was mixed with 92 parts water, and acrylonitrile was intermittently added dropwise thereto, under stirring, at a rate of 2 parts per hour while controlling pH at 8.0 with 0.5 N KOH aqueous solution to react at 10° C. for 6 hours. The reaction proceeded almost quantitatively to obtain 110 parts of a 14.5% acrylamide aqueous solution. Then, this solution was concentrated under reduced pressure at a temperature of not higher than 35° C. to obtain 53.2 parts of a 30% acrylamide aqueous solution. When polymerization of acrylamide in the solution was checked by adding methanol thereto, almost no white turbidity was observed. Thus, it was identified as a polymer-free, stable aqueous solution of acrylamide monomer.

On the other hand, a cell-free, 14.5% acrylamide aqueous solution obtained for comparison by reacting under the same conditions as in Example 1 except omitting the treatment with dialdehyde was colored considerably dark yellow and, during concentration, the viscosity of the solution increased and, in the end, the whole solution became a gel-like polymer. Thus, this acrylamide aqueous solution could not be concentrated.

EXAMPLE 2 AND COMPARATIVE EXAMPLE 2

40 parts of washed microbial cells (water content: 75%) of strain N-774 prepared by aerobic culture in the same manner as in Example 1, 4.5 parts of acrylamide, 0.5 part of N,N'-methylenebisacrylamide, and 40 parts of a 0.05 M phosphate buffer solution (pH: 8.0) were mixed to obtain a uniform suspension. Then, 5 parts of a 5% dimethylaminopropionitrile aqueous solution and 10 parts of a 2.5% potassium persulfate aqueous solution were added thereto, and the resulting mixture was maintained at 10° C. for 1 hour to polymerize and gel. Thus obtained cell-containing gel was pulverized into small particles, and mixed with 200 parts of a 0.05 M phosphate buffer (pH: 8.0) and 0.4 part of a 50% glutaraldehyde aqueous solution to react at 10° C. for 1 hour. After completion of the reaction, the small particles of cell-containing gel were washed with a 0.05 M phosphate buffer to prepare dialdehyde-treated immobilized cells.

20 g of the immobilized cells were filled in a jacketed column (3 cm in inside diameter and 25 cm in length) and a 4% acrylonitrile aqueous solution (using a 0.05 M phosphate buffer; pH: 8.0) was allowed to flow downward from the upper part of the column at a rate of 25 ml/hr at 10° C. to react. In this occasion, the effluent from the lower part of the column was smoothly obtained without polymerization for a long time. This effluent contained 5.3% acrylamide, and no acrylonitrile was detected therein. On the other hand, when the same experiment was conducted for comparison except using immobilized cells not treated with the dialdehyde, the effluent became viscous about three hours after beginning of the reaction, and polymerization of produced acrylamide prevented smooth operation.

EXAMPLE 3 AND COMPARATIVE EXAMPLE 3

40 parts of washed microbial cells of strain N-774 obtained by aerobic culture in the same manner as in Example 1, 9 parts of acrylamide, 1 part of methylenebisacrylamide, 0.8 part of a 40% glyoxal aqueous solution, and 34.2 parts of a 0.05 M phosphate buffer (pH: 8.0) were mixed to prepare a uniform suspension, and stirred at 10° C. for 1 hour to conduct the treatment with the dialdehyde. Subsequently, 5 parts of a 5% dimethylaminopropionitrile aqueous solution and 10 parts of a 2.5% potassium persulfate aqueous solution were added to this suspension to cause polymerization and gelation. After standing for 1 hour, the resulting cell-containing gel was pulverized into small particles and washed with a 0.05 M phosphate buffer to obtain 100 parts of dialdehyde-treated immobilized cells. 20 g of the resulting cells were filled in a jacketed column (3 cm in inside diameter and 25 cm in length) and a 4% acrylonitrile aqueous solution was continuously allowed to flow down at a rate of 25 ml/hr from the upper part of the column at 10° C. to conduct the reaction. In this occasion, the effluent from the lower part of the column was smoothly obtained with no polymerization for a long time. The effluent obtained 100 hours after beginning of the reaction contained 5.3% acrylamide, and no acrylonitrile was detected. On the other hand, when the same experiment was conducted for comparison except omitting the treatment with the dialdehyde, the effluent became viscous about 5 hours after beginning of the reaction and polymerization of produced acrylamide prevented smooth operation of the continuous column process.

EXAMPLE 4 AND COMPARATIVE EXAMPLE 4

40 parts of washed microbial cells of strain N-774 obtained by aerobic culture in the same manner as in Example 1 was mixed with 0.2 part of a 50% glutaraldehyde aqueous solution and 59.8 parts of a 0.05 M phosphate buffer (pH: 8.0), and stirred at 10° C. for 1 hour to react. Thus the treatment with dialdehyde was conducted. After completion of the reaction, the cell suspension was centrifuged, and the cells were washed twice with a 0.05 M phosphate buffer (pH: 8.0), then again centrifuged to obtain about 40 parts of a dialdehyde-treated cell paste (water content: 75%).

92 parts of water was added to 8 parts of the cells, and methacrylamide was intermittently added dropwise thereto at a rate of 3 parts per hour under stirring while controlling pH to 8.0 with 0.5 N KOH, and the reaction was conducted at 10° C. for 5 hours. After completion of the reaction, cells were removed by centrifugation to obtain 107 parts of a slightly yellow aqueous solution containing 16.8% methacrylamide. Subsequently, this solution was concentrated at not higher than 40° C. under reduced pressure to obtain a 25% methacrylamide aqueous solution. When methanol was added to the concentrate to check information of a methacrylamide polymer in the solution, there was observed almost no white turbidity due to the polymer.

On the other hand, a methacrylamide aqueous solution obtained for comparison by reacting in the same manner under the same conditions as in Example 4 was colored dark yellow and, when concentrated as such under reduced pressure, this aqueous solution underwent polymerization to form a gel. Thus, concentration of the solution was impossible.

EXAMPLE 5 AND COMPARATIVE EXAMPLE 5

50 parts of washed microbial cells (water content: 80%) of each of strain N-771 of the genus Corynebacterium, strain N-775 of the genus Nocardia and strain CBS 717.73 of the genus Brevibacterium described in U.S. Pat. No. 4,001,081 obtained by aerobic culture in the same manner as in Example 1 was mixed with 0.2 part of a 50% glutaraldehyde aqueous solution and 10 parts of a 0.05 M phosphate buffer (pH: 8.0), and stirred at a temperature of 10° C. or less for 1 hour to react. Thus the treatment with dialdehyde for each was conducted. Subsequently, 9.5 parts of acrylamide, 34.8 parts of a 0.05 M phosphate buffer (pH: 8.0) containing 0.5 part of methylenebisacrylamide, 5 parts of a 5% dimethylaminopropionitrile aqueous solution and 10 parts of a 2.5% potassium persulfate aqueous solution were added to each resulting suspension. Each suspension was maintained at 10° C. or less for 1 hour to cause polymerization and gelation. Each resulting cell-containing gel was pulverized into small particles about a diameter of 2 mm and washed with a 0.05 M phosphate buffer to obtain 100 parts of dialdehyde-treated immobilized cells. Then, 20 g of each resulting immobilized cells was filled in a jacketed column (3 cm in inside diameter and 25 cm in length), and a 4% acrylonitrile aqueous solution (using a 0.05 M phosphate buffer; pH: 8.0) was continuously allowed to flow down through the column at a rate of 10 ml/hr from the upper part of the column at 10° C. to conduct the reaction. On this occasion, each effluent from the lower part of the column was smoothly obtained with no polymerization for a long time. Each of the resulting effluents contained 5.3% acrylamide and no acrylonitrile was detected therein. On the other hand, when the same experiment was conducted for comparison using immobilized cells not treated with the dialdehyde, each effluent became viscous about 5 hours or less after beginning of the effusion of the reaction solution from the lower part of the column, and the polymerization of acrylamide produced with each strain prevented smooth operation of the continuous column process.

While the invention has been described in detail and with reference to specific embodiments thereof, it will be apparent to one skilled in the art that various changes and modifications can be made therein without departing from the spirit and scope thereof.

What is claimed is:

1. A process for producing a stable aqueous solution of acrylamide or methacrylamide by subjecting acrylonitrile or methacrylonitrile in water to the action of microorganisms having a nitrilasic activity, selected from the genus Corynebacterium, the genus Nocardia, the genus Bacillus, and genus Bacteridium in the sense of Prevot, the genus Micrococcus or the genus Brevibacterium in the sense of Bergey, which comprises treating said microorganisms with a water soluble dialdehyde before reaction with the nitrile to thereby inhibit polymerization of the acrylamide or methacrylamide produced.

2. The process of claim 1, wherein said microorganisms having a nitrilasic activity are immobilized with an acrylamide series polymer before or after the treatment with said water-soluble dialdehyde.

3. The process of claim 1, wherein said dialdehyde is glyoxal.

4. The process of claim 1, wherein said dialdehyde is glutaraldehyde.

5. The process of claim 1, wherein said microorganism is selected from the group consisting of strain N-771 of the genus Corynebacterium, strain N-774 of the genus Corynebacterium, and strain N-775 of the genus Nocardia.

6. The process of claim 1, wherein said process is a continuous column process.

7. The process of claim 1, wherein said dialdehyde has a solubility of at least 5% in water at 20° C.

8. The process of claim 1, wherein said microorganisms are selected from the group consisting of strains registered at the CBS under the numbers C 211 CBS 499.74, R 312, CBS 717.73, B 222 CBS 498.74, A111 CBS 497.74, R 341 CBS 496.74, R 340 CBS 495.74 R 332 CBS 494.74.

9. The process of claim 1, wherein said microorganisms are strain CBS 717.73 of the genus Brevibacterium.

* * * * *